United States Patent [19]

Otto et al.

[11] Patent Number: 5,382,236
[45] Date of Patent: Jan. 17, 1995

[54] IMPLANTABLE INFUSION PUMP

[75] Inventors: Karl-Heinz Otto; Gerd Pfister, both of Kiel, Germany

[73] Assignee: Anschütz & Co., GmbH, Germany

[21] Appl. No.: 934,520

[22] PCT Filed: Nov. 29, 1991

[86] PCT No.: PCT/DE91/00944
§ 371 Date: Jun. 14, 1993
§ 102(e) Date: Jun. 14, 1993

[87] PCT Pub. No.: WO92/09316
PCT Pub. Date: Jun. 11, 1992

[30] Foreign Application Priority Data

Nov. 29, 1990 [DE] Germany ............... 4038049

[51] Int. Cl.⁶ ............................................. A61M 31/00
[52] U.S. Cl. ................................. 604/141; 604/891.1
[58] Field of Search ................ 604/141, 891.1, 890.1

[56] References Cited

U.S. PATENT DOCUMENTS

| | | | |
|---|---|---|---|
| 4,299,220 | 11/1981 | Dorman | 604/141 |
| 4,360,019 | 11/1982 | Portner et al. | 604/141 |
| 4,496,343 | 1/1985 | Prosl et al. | 604/141 |
| 4,673,391 | 6/1987 | Kondo et al. | 604/141 |
| 4,714,462 | 12/1987 | DiDomenico | 604/141 |
| 4,784,648 | 11/1988 | Singh et al. | 604/141 |
| 4,931,050 | 6/1990 | Idriss | 604/141 |
| 4,955,861 | 9/1990 | Enegren et al. | 604/141 |
| 5,067,943 | 11/1991 | Burke | 604/141 |

Primary Examiner—Paul J. Hirsch
Attorney, Agent, or Firm—Herbert W. Larson

[57] ABSTRACT

An infusion pump with a flexible medication container, a chamber containing a $C_2 Cl_2 F_4$ propellant gas acting upon the medication container and a capillary tube acting as a choke. The propellant gas chamber accommodates a pressure of 2.5 bar over atmospheric.

4 Claims, 1 Drawing Sheet

IMPLANTABLE INFUSION PUMP

This application is a continuation of parent international application PCT/DE91/00944, filed Nov. 29, 1991 and German P 4038049.1 filed Nov. 29, 1990.

BACKGROUND OF THE INVENTION

The invention relates to an implantable infusion pump with an elastic medicament container, a propellant chamber acting on the latter and having a propellant formed from a chlorofluorohydrocarbon, as well as a restricting capillary tube.

Implantable infusion pumps are used for the long-term administration of medicaments, e.g. morphine in a constant dose over a long period. Compared with conventional injections, they offer the advantage that it is no longer necessary to overdose to such an extent that despite the breaking down of the medicament up to the next adminstration time there is no drop below a certain minimum dose and instead there is a uniform and significantly reduced supply of the medicament.

However, hitherto in the case of infusion pumps of the aforementioned type problems have occurred when the temperature was changed. If the person with such an infusion pump implanted has fever with a body temperature of 42° C., as a result of the additional expansion of the propellant the delivery can be up to 46% more (propellant: trichlorofluoromethane), which is naturally highly undesired.

Similar problems can occur when the atmospheric pressure is changed. Here, e.g. when staying at an altitude of 3000 m, which roughly corresponds to atmospheric pressure and which can occur in an aircraft, there can even be an additional delivery of 55%.

The problem of the invention is therefore to provide an implantable infusion pump, in which such effects play a very minor part and the operational reliability of the pump is improved.

SUMMARY OF THE INVENTION

According to the invention this problem is solved in that the propellant chamber is designed for a filling pressure of more than 2.5 bar above atmospheric pressure and the propellant is 1,2-dichlorotetrafluoroethane ($C_2Cl_2F_4$). For this purpose said propellant has a very suitable vapour pressure curve and is non-toxic, i.e. harmless, if it comes into contact with the body.

It is also proposed that the medicant container is formed from a metal diaphragm corrugated bellows. Once again the latter is preferably made from titanium. This material is light, chemically resistant, sufficiently impervious and mechanically very robust.

DETAILED DESCRIPTION OF THE INVENTION

Figure 1:
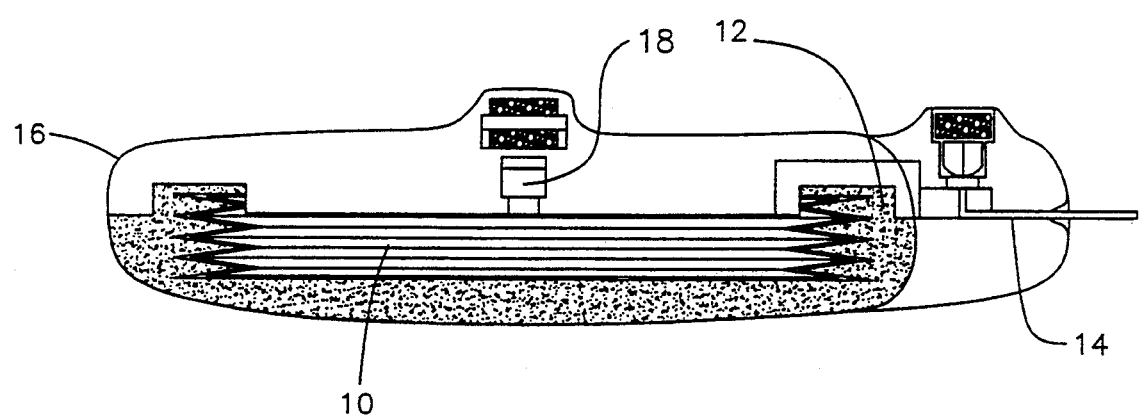
FIG. 1 is a sectional elevational view of the implantable infusion pump of the invention.

According to a preferred development an outer container receives the propellant chamber and the medicament container. This outer container is also made from titanium. This offers the same advantages as for the medicament container and additionally also the high biocompatibility of titanium.

The invention is described in greater detail hereinafter relative to the single drawing, which is a sectional view of an implantable infusion pump. The infusion pump comprises an outer container 16 in which is formed a medicament container 10 as a metal diaphragm corrugated bellows, a propellant chamber 12, a capillary tube 14 for restricting the medicament flow and a septum 18, which is used for the supply of the medicament by a doctor with the aid of a syringe and a special needle.

The complete pump shown is implanted in a patient, preferably in the abdominal region. From the infusion pump passes a catheter to the point where medicament administration is to take place, e.g. at the vertebral column.

As a function of the chosen delivery and the pump size, it only has to be filled at long intervals of typically one month. For this purpose use is made of special needles, which can pass in non-cutting manner through the septum 18, which is a type of cork.

Due to the fact that the propellant in under high pressure, temperature changes only have half the effect with the chosen propellant compared with the previous situation and pressure fluctuations can even only represent roughly a quarter of the previously attainable tolerances in the delivery.

A further highly desired effect is that, apart from the precise dosing, the high pressure leads to increased operational security, because the capillary tube is subject to a higher pressure and particles in the medicament can disturb the flow to a lesser extent.

A membrane filter is provided between the medicament container and the capillary tube and is carried by a support screen.

For strength reasons and because the material is chemically very resistant and biocompatible and also very light, titanium is used for all parts where stability is important.

The outer container 16 directly forms the propellant chamber 12, i.e. the pressure container for the propellant. On filling the medicament container 10 it will expand in the propellant chamber 12 and liquefy the propellant. Conversely the propellant is only very slowly reconverted into the gaseous phase, when more space is made available to it through the expelled medicament.

We claim:

1. In an infusion pump for implanting within the body of a patient, the pump including an outer housing enclosing a propellant chamber and an elongated inner housing containing a medication, the propellant chamber containing at least 2.5 bar over atmospheric pressure of a propellant gas, a capillary tube of restricted diameter leading out of the inner housing for restricting the medication flow and a means for filling the inner housing with the medication, the improvement comprising the housing containing the medication is elastic, and the propellant is dichlorotetrafluoroethane to cause a minimal flow rate change for the medication to be infused when pressure or temperature in the patient changes.

2. The infusion pump according to claim 1 wherein the elastic elongated inner housing is a metal membrane corrugated bellows.

3. The infusion pump according to claim 2 wherein the metal membrane is made from titanium.

4. The infusion pump according to claim 1 wherein the outer housing is made from titanium.

* * * * *